United States Patent [19]
Sackner et al.

[11] Patent Number: 5,588,425
[45] Date of Patent: Dec. 31, 1996

[54] METHOD AND APPARATUS FOR DISCRIMINATING BETWEEN VALID AND ARTIFACTUAL PULSE WAVEFORMS IN PULSE OXIMETRY

[75] Inventors: Marvin A. Sackner, Miami Beach; Dana M. Inman, Miami, both of Fla.

[73] Assignee: Nims, Incorporated, Miami Beach, Fla.

[21] Appl. No.: 431,469

[22] Filed: May 1, 1995

Related U.S. Application Data

[63] Continuation of Ser. No. 66,593, May 21, 1993, abandoned.

[51] Int. Cl.$^6$ ................................................... G06F 15/42
[52] U.S. Cl. .......................................... 128/632; 128/700
[58] Field of Search ..................... 128/632–635, 128/670, 671, 696, 700, 703, 704, 706, 708, 715, 664, 665; 356/39, 40, 41; 607/25; 364/413.03, 413.09

[56] References Cited

U.S. PATENT DOCUMENTS

| | | | |
|---|---|---|---|
| 4,446,872 | 5/1984 | Marsoner et al. | 128/700 |
| 4,546,777 | 10/1985 | Groch et al. | 128/715 |
| 4,548,204 | 10/1985 | Groch et al. | 128/700 |
| 4,549,552 | 10/1985 | Groch et al. | 128/700 |
| 4,800,495 | 1/1989 | Smith | 364/413.03 |
| 4,819,752 | 4/1989 | Zelin | 128/633 |
| 4,863,265 | 9/1989 | Flower et al. | 356/41 |
| 4,867,571 | 9/1989 | Frick et al. | 128/633 |
| 4,911,167 | 3/1990 | Corenman et al. | 128/633 |
| 4,928,692 | 5/1990 | Goodman et al. | 128/633 |
| 4,955,379 | 9/1990 | Hall | 128/633 |
| 5,025,791 | 6/1991 | Niwa . | |
| 5,036,857 | 8/1991 | Semmlow et al. | 128/715 |
| 5,099,841 | 3/1992 | Heinonen et al. | 128/670 X |
| 5,111,817 | 5/1992 | Clark et al. . | |
| 5,299,120 | 3/1994 | Kaestle | 364/413.09 |

FOREIGN PATENT DOCUMENTS

0262778A1  4/1988  European Pat. Off. .......... A61B 5/00

OTHER PUBLICATIONS

*Knowing Your Monitoring Equipment*, Michael W. Wukitsch, et al., Pulse Oximetry: Analysis of Theory, Technology, and Practice, Little Brown and Company, pp. 290–301 (1988).

*Chest*, Schnapp, Lynn M. et al., Pulse Oximetry: Uses and Abuses, Nov. 1990; 98:1244–50.

*Anesth Analg*, Alexander, Christian M. et al., Principles of Pulse Oximetry: Theoretical and Practical Considerations, 1980, 68:368–76.

*Primary Examiner*—Angela D. Sykes
*Assistant Examiner*—Samuel Gilbert
*Attorney, Agent, or Firm*—Cohen, Pontani, Lieberman, Pavane

[57] ABSTRACT

A method and apparatus for use in pulse oximetry for discriminating between valid pulse waveforms and artifactual pulse waveforms. Systolic upstroke times for valid pulse waveforms are in a consistent, narrow range which varies only slightly from subject to subject. This narrow range, which may be defined empirically for each subject or established by a default setting applicable to all subjects, defines a predetermined range of systolic upstroke times indicative of valid pulse waveforms. The systolic upstroke time of each pulse waveform is compared against the predetermined range, and pulse waveforms are deemed valid only if their systolic upstroke times are within the predetermined range. Only arterial oxygen saturation levels based on validated pulse waveforms are accepted. The present invention may also be used to validate the heart rate and/or R-R intervals of an ECG, and for discriminating between sleep and wakefulness in a monitored subject.

29 Claims, 13 Drawing Sheets

NORMAL OXIP

STABLE OxIP

NORMAL OXIP IN PRESENCE OF PERIODIC BREATHING

FIG. 6   CORRECT OXIP DETECTION DESPITE AMPLITUDE VARIATIONS

FIG. 7  VALIDITY OF O2 SAT WITH MARKED BODY MOVEMENTS (VT & IMP)

MAJOR O2 DESATURATION

FALSE BRADYCARDIA: LOW AMPLITUDE ECG

TRUE & FALSE BRADYCARDIA (B)

METHOD AND APPARATUS FOR DISCRIMINATING BETWEEN VALID AND ARTIFACTUAL PULSE WAVEFORMS IN PULSE OXIMETRY

This is a continuation of application Ser. No. 08/066,593, filed May 21, 1993 now abandoned.

BACKGROUND OF THE INVENTION

1. Field of the Invention

This invention pertains to pulse oximetry, and more particularly to discrimination between valid and artifactual pulse waveforms obtained by pulse oximetry.

2. Prior Art

Commercially available pulse oximeters provide instantaneous in vivo measurements of arterial oxygenation by determining the color of blood between a light source and a photodetector. To distinguish between the two main types of hemoglobin, i.e., oxyhemoglobin and reduced hemoglobin, measurement of light absorption is carried out at two wavelengths using a light source that consists of two different light emitting diodes, one for red and the other for infrared light. With each cardiac cycle, there is cyclic light absorption by tissue beds. During diastole, absorption is a result of venous blood, tissue, bone and pigments (melanin, nail polish, etc.). During systole, light absorption is increased by influx of arterialized blood into the tissue bed. The oximeter determines the difference between background absorption during diastole and peak absorption during systole at both red and infrared wavelengths, as this difference corresponds to the absorption caused by arterialized blood. Since oxygen saturation determines the red:infrared light absorption ratio, differences in this ratio are used to compute the arterial oxygen saturation, a value derived empirically by the manufacturer's calibration curve. See, e.g. Schnapp, et al., *Pulse Oximetry: Uses and Abuses*, Chest 1990; 98: 1244–1250.

Accurate measurement of arterial oxygen saturation is highly dependent upon a valid pulse waveform, typically detected by a sensor disposed on an extremity or, in the case of adults, on the nose or ear. However, the pulse waveform can be distorted, rendering corresponding arterial oxygen saturation values invalid. For example, the pulse waveform can be distorted by vasoconstriction associated with hypotension or motion of the body site where the sensor is affixed. To verify the validity of the pulse waveform, some pulse oximeters display the pulse waveform in real time so the operator call judge whether a valid waveform is present. Others use the electrical amplitudes of the waveform as a guide to waveform validity and display a message if artifacts are present. For example, the amplitude of the varying component of the pulse waveform (AC) may be compared against the background light absorption (DC) or an arbitrary value. It has been suggested that the pulsatile strength is adequate and hence the pulse waveform valid when the AC/DC ratio exceeds 0.2%, but this standard has not been validated. At least one manufacturer of pulse oximeters employs an autogain program to flesh out low amplitude pulse waveforms for display when the AC/DC ratio falls below 0.2%. However, arterial oxygen saturation values at signal strengths below this threshold may still be valid provided the pulse waveform has a normal configuration. See, e.g. Wukitsch, et al., *Pulse Oximetry: Analysis of Theory, Technology, and Practice*, J. Clin. Monit. 1988; 4: 290–301.

At least one manufacturer of pulse oximeters has approached the motion artifact problem by synchronizing data acquisition by the pulse oximeter with the R wave of an EGG. However, the oximeter may synchronize with EGG artifacts caused by motion or shivering, resulting in erroneous readings. Furthermore, with this approach the pulse rate displayed by the oximeter is necessarily equal to the heart rate derived from the EGG, thereby eliminating concordance of pulse oximeter pulse rate with ECG heart rate as a validator of pulse oximetry data. See Alexander, et al., *Principles of Pulse Oximetry: Theoretical and Practical Considerations*. Anesth. Analg. 1989; 68: 368–376. This technique may also be subject to error because of the variability in operator and/or computer selection of peak to peak and trough to trough points of the pulse waveform, as well as inherent errors related to sampling rates, all of which affect the calculation of arterial saturation values.

U.S. Pat. No. 5,025,791 proposes detecting artifactual pulses by incorporating a motion detector in the pulse oximeter sensor. This, of course, requires the incorporation of additional components in the pulse oximeter sensor, as well as additional circuitry for processing the information derived from the motion sensor. U.S. Pat. No. 4,955,379 proposes eliminating artifactual pulse waveforms by employing a band pass filter.

Pulse oximeters have analog or digital outputs for values of arterial oxygen saturation as well as for pulse waveforms, and these outputs can be recorded and displayed on polygraph recorders and/or digital computers. These recordings can then be reviewed and correct values of arterial oxygen saturation recognized from the appearance of the pulse waveform, i.e. if the pulse waveform is correctly configured the corresponding arterial oxygen saturation value is accepted, whereas if the waveform is perceived as artifactual, the arterial oxygen saturation value is rejected. However, with lengthy recordings as in overnight studies in adults or babies, visual scanning is impractical due to time constraints, since as many as 20,000 to 80,000 or more pulse waveforms may be collected.

In view of the above, there is a need for confidently assessing the validity of arterial oxygen saturation measurements obtained with pulse oximetry, preferably in real time, and particularly for monitoring long term trends, as in critically ill patients.

It is accordingly an object of the present invention to provide a method and apparatus for validating arterial oxygen saturation measurements obtained with pulse oximetry.

It is another object of the invention to provide a method and apparatus for verifying arterial oxygen saturation measurements derived from pulse oximetry by verifying the validity of the pulse waveforms detected by a pulse oximetry sensor.

It is a further object of the present invention to provide a method and apparatus of the aforementioned type which discriminates between valid and invalid pulse waveforms on a real time basis.

It is yet a further object of the present invention to provide a method and apparatus of the aforementioned type which is highly accurate in its discrimination between valid and invalid pulse waveforms, even in the case of low amplitude pulse waveforms.

SUMMARY OF THE INVENTION

The method and apparatus of the present invention verifies the validity of pulse waveforms obtained with pulse oximetry by detecting the systolic upstroke time for each pulse waveform, i.e. the time from onset of systole to peak, comparing the detected systolic upstroke time to a predetermined range of values indicative of valid pulse waveforms, and then rejecting pulse waveforms with systolic upstroke times outside the range. Only arterial saturation values computed by the oximeter from pulse waveforms validated in accordance with the method and apparatus of the present invention are accepted.

The present invention is based upon the recognition that the systolic upstroke time for pulse waveforms derived from pulse oximetry falls within a consistent, narrow range from subject to subject, including infants, children and adults. In utilizing the present invention on a subject, initially a small number of pulse waveforms, for example those derived over a period of a few minutes, may be validated as "correct" pulse waveforms uncontaminated with motion artifacts by, for example, visual analysis. Once validated, the median or mean of the systolic upstroke time for these pulse waveforms can be computed, as by the microprocessor within the pulse oximeter, or by an independent digital computer connected to the analog or digital output of the pulse oximeter. From this median or mean, a range of acceptable systolic upstroke times is derived, i.e. values deviating from the median or mean by less than an amount indicative of an invalid pulse waveform. The range, for example, may be a fixed time interval based upon empirical observation, within 2 SD of the median or mean, within the 2%–98% quartertile distance, etc. This range of systolic upstroke times can then be input, e.g. using the keyboard on the independent digital computer, to the microprocessor within the pulse oximeter or to the digital computer itself. Then, as new pulse waveforms are collected from the pulse oximeter, their systolic upstroke times are compared with the predetermined range of acceptable values, and arterial oxygen saturation values are displayed and/or stored only if the systolic upstroke time of the respective pulse waveform falls within the predetermined range.

Pulse waveforms for which the systolic upstroke time falls outside of the predetermined range are considered distorted by motion artifact and the corresponding arterial oxygen saturation levels are rejected. Since it is accepted that skeletal muscles are inactive during sleep, the rejected waveforms indicative of motion artifact may be used to distinguish wakefulness from sleep in a manner analogous to actigraphs.

Broadly speaking, the present invention is a method for detecting artifactual pulse waveforms in pulse oximetry comprising measuring one of the systolic upstroke time and the diastolic time of pulse waveforms generated by a pulse oximeter monitoring a subject, comparing the selected one of the measured systolic upstroke time and diastolic time to a predetermined range of systolic upstroke times and diastolic times, respectively, indicative of a correct pulse waveform, and rejecting as artifactual pulse waveforms wherein the selected one of the measured systolic upstroke time and the diastolic time is outside its respective predetermined range. Preferably, the selected one of the systolic upstroke time and the diastolic time is the systolic upstroke time, as diastolic time varies with cardiac arrhythmia whereas systolic upstroke times do not. In accordance with the invention, only arterial oxygen saturation levels derived by the oximeter from non-rejected pulse waveforms are accepted.

The method of the present invention further comprises monitoring the subject with an ECG for generating a signal indicative of the subject's heart rate, determining the pulse rate of the pulse waveforms generated by the pulse oximeter, and validating the subject's heart rate only when the pulse rate or non-rejected pulse waveforms is approximately equal to the heart rate.

The present invention also comprises an apparatus for detecting artifactual pulse waveforms in pulse oximetry comprising means for measuring one of the systolic upstroke time and the diastolic time of pulse waveforms generated by a pulse oximeter monitoring a subject, means for comparing the selected one of the measured systolic upstroke time and the diastolic time to a predetermined range of systolic upstroke times and diastolic times, respectively, indicative of a correct pulse waveform, and means for rejecting as artifactual pulse waveforms wherein the selected one of the measured systolic upstroke time and the diastolic time is outside its respective predetermined range.

The apparatus of the present invention further comprises an ECG for generating a signal indicative of the subject's heart rate, means for determining the pulse rate of the pulse waveforms generated by the pulse oximeter, and means for indicating that the pulse rate of non-rejected pulse waveforms is approximately equal to the heart rate.

These as well as further features and advantages of the present invention will be more fully apparent from the following detailed description and annexed drawings of a presently preferred embodiment thereof.

DETAILED DESCRIPTION OF THE PREFERRED EMBODIMENTS

Figure 1:
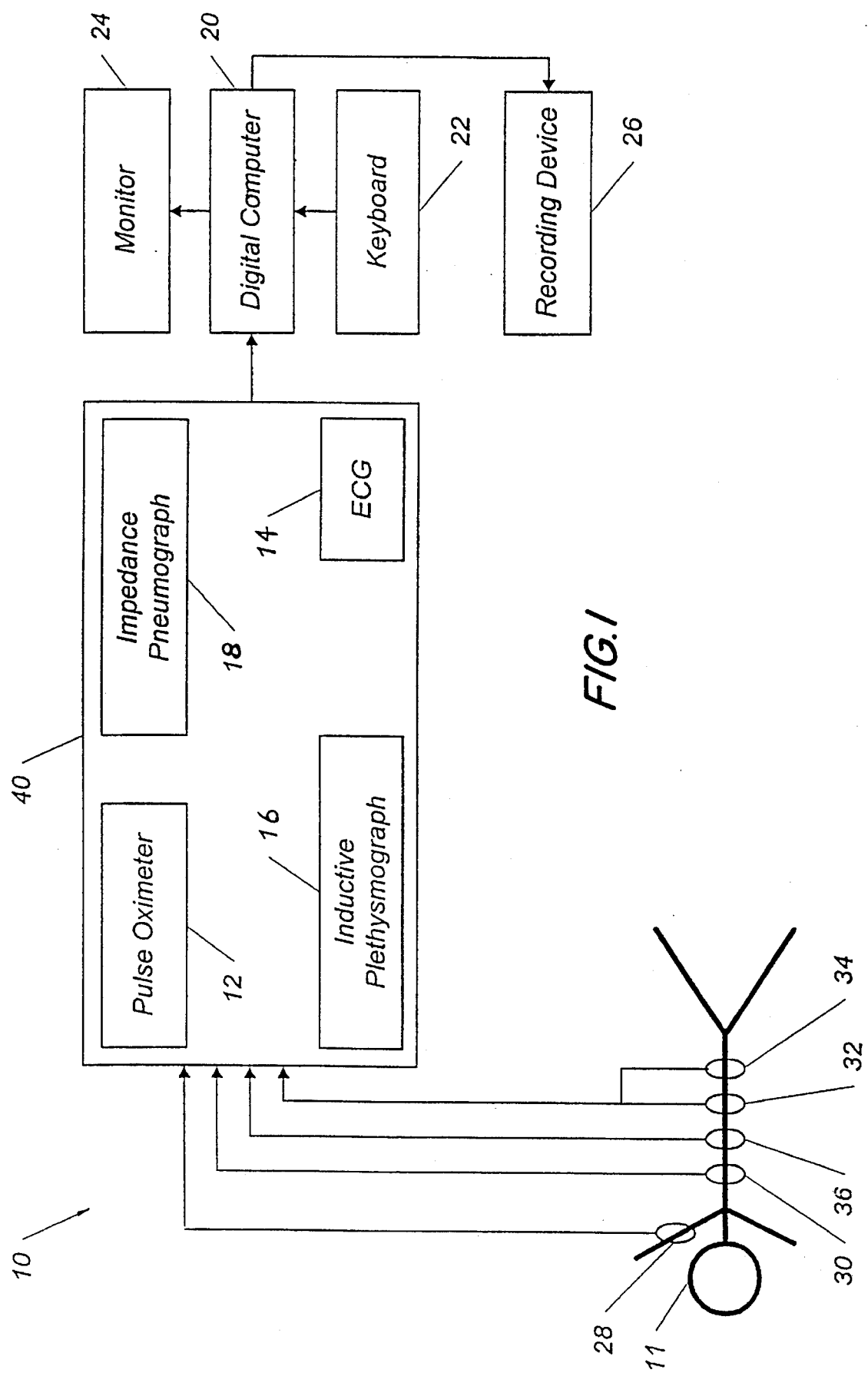
FIG. 1 is a diagrammatic representation of an apparatus in accordance with the present invention.

Referring now to the drawings, and initially to FIG. 1 thereof, an apparatus in accordance with the present invention is generally designated at 10. As noted above and explained more fully below, the primary purpose of the present invention is to confirm the validity of arterial oxygen saturation measurements derived from pulse oximetry. As shown, the apparatus 10 includes a pulse oximeter 12, an ECG 14, an inductive plethysmograph 16, an impedance pneumograph 18, a digital computer 20 having the usual keyboard 22 and monitor 24, and a recording device 26 for generating recordings of data output by the computer 20. While the pulse oximeter 12, ECG 14, inductive plethysmograph 16 and impedance pneumograph 18 may comprise conventional discrete devices, as presently preferred and diagramatically illustrated in FIG. 1, a Respitrace PT, which incorporates the functionality of all four devices, is preferably employed in lieu of discrete devices. The Respitrace PT, designated at 40, is commercially available from Non-Invasive Monitoring Systems, Inc., the assignee of the present invention.

Still referring to FIG. 1, a number of sensors are secured to the patient 11 for inputting data to the Respitrace PT. In particular, the apparatus 10 includes a conventional pulse oximetry sensor 28 secured, for example, to the toe of the patient 11, a conventional ECG sensor 30 secured to the chest of the patient 11, conventional inductive plethysmographic thoracic and abdominal sensors 32 and 34, and a conventional impedance pneumographic sensor 36 secured to the patient's chest. The Respitrace PT 40 processes data from its various inputs using RespiEvents, a software program available from Non-Invasive Monitoring Systems, Inc., for generating data of the type depicted in the 12 waveforms in each of FIGS. 2–13. In accordance with the apparatus 10 shown in FIG. 1, the data from the Respitrace PT is downloaded to a removable hard drive which is then transferred to the computer 20 for generating hard copy recordings on the device 26. As will become more fully apparent as this description progresses, the apparatus 10 and the waveforms depicted in FIGS. 2–13 sere primarily to validate the methodology of the present invention. In actual use of the invention, therefore, the apparatus 10 may be substantially simplified, as more fully explained below.

In the waveforms of FIGS. 2–13, the abscissa depicts the time lapse in seconds or minutes. The 12 depicted waveforms in each of FIGS. 2–13 have the following significance: (1) ECG is the output waveform of the electrocardiogram 14; (2) R-R represents the interval between successive R-wave peaks as detected as by the R-wave trigger of the ECG, with the amplitude of the spikes denoting the R-R interval in milliseconds; (3) HR is the heart rate in beats per minute as computed from the R-R intervals of the ECG; (4) PR is the pulse rate as detected from the pulse waveform output from the pulse oximeter 12, also given in beats per minute; (5) OxiP is the analog representation of the pulse waveform output from the pulse oximeter 12, with the ordinate denoting amplitude in arbitrary units; (6) Sy is the systolic upstroke time of the pulse waveform OxiP, i.e. the time interval from the onset of systolic upstroke to peak systolic upstroke as derived from the OxiP waveform and shown, by way of example, as the time interval $\Delta t$ in the seventh pulse waveform in FIG. 2, the ordinate denoting units of time, i.e. seconds, for each successive pulse; (7) Di is the diastolic time interval of the pulse waveform OxiP, i.e. the time interval from systolic peak to the trough of the pulse waveform, with the ordinate again denoting seconds; (8) SaO2 is the analog representation of the signal output from the pulse oximeter 12 indicative of the arterial oxygen saturation as measured by the pulse oximeter 12 from the signals received via the pulse oximetry sensor 28, and given as a percentage of the total hemoglobin in a subject's blood which is bound to oxygen, such oxygen-bound hemoglobin being known as oxyhemoglobin; (9) PG ("pulse good") is all indication of whether or not the pulse waveform OxiP is validated in accordance with the present invention, the ordinate for the PG waveform comprising a binary logic, with 1 denoting a good pulse and a 0 denoting a rejected pulse; (10) Mvmnt is an indicator of movement of the body area where the pulse oximetry sensor 28 is placed, as confirmed by the presence of invalid or rejected pulses for a complete breath, the ordinate for this waveform also being a binary logic, with 1 denoting movement and 0 denoting no movement; (11) Vt is the tidal volume for the subject 11 as measured by the inductive plethysmographic sensors 32, 34 given as a percentage of a base line tidal volume; and (12) Imp is the output waveform from the impedance pneunographic sensor 36, with the ordinate denoting amplitude in arbitrary units.

Figure 2:
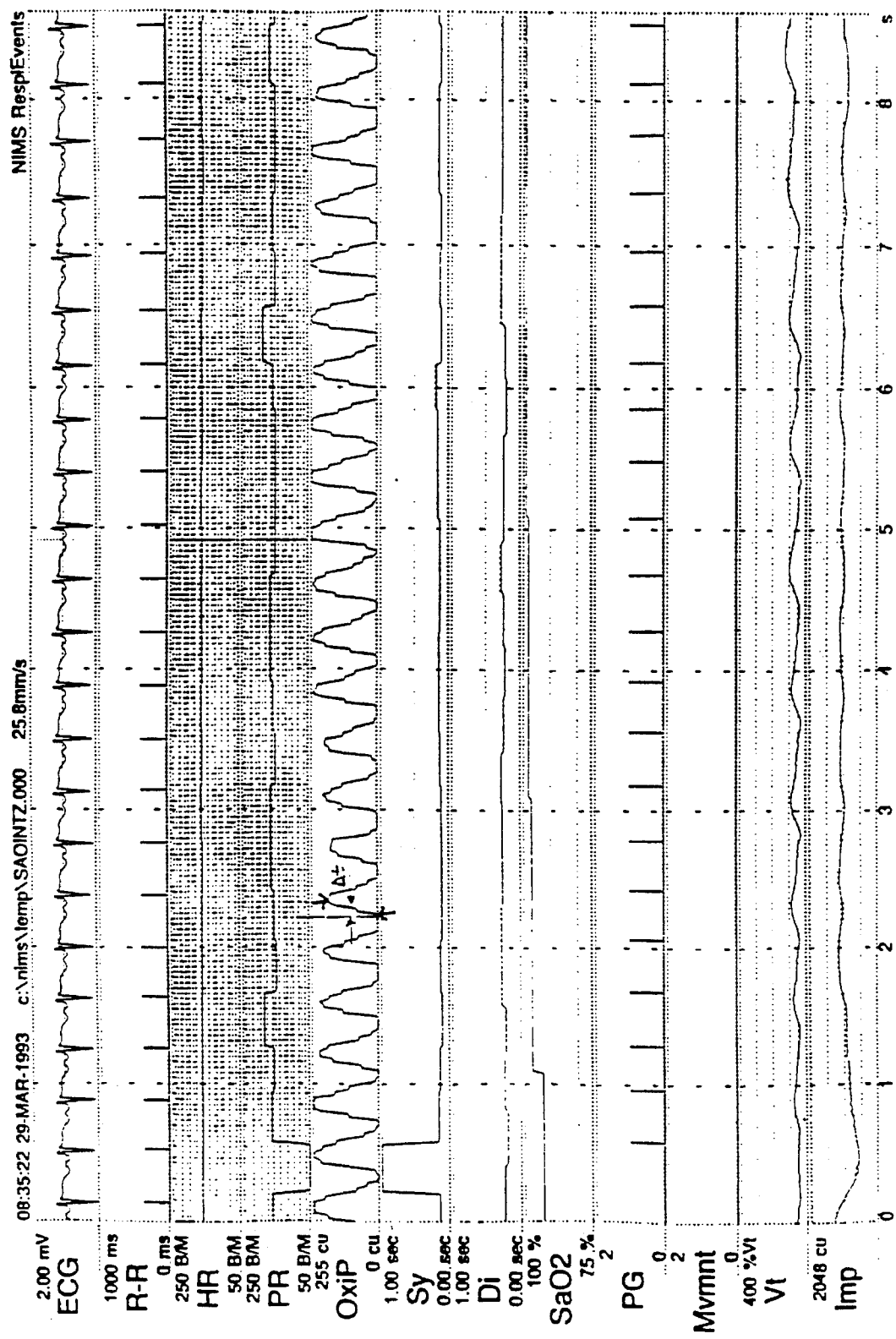
FIGS. 2–13 are polygraphic recordings illustrating the methodology of the present invention.

In accordance with the present invention, the systolic upstroke time Sy, the diastolic time Di and the pulse rate PR are computed by the RespiEvents program from the pulse waveform OxiP computed by the pulse oximeter 12 of to the Respitrace PT from the signals received by the pulse oximeter 12 from the sensor 28. Referring to FIG. 2, which is a time plot of about 8.5 seconds duration, the systolic upstroke time Sy is displayed as a continuous waveform and, as noted earlier, represents the time interval between the onset of systole and peak, shown by way of example as $\Delta t$ on the seventh pulse waveform OxiP in FIG. 2. The artifact in the leftmost portion of the Sy tracing in FIG. 2 is an initialization artifact. After this artifact, it may be seen that the systolic upstroke time Sy is relatively stable from pulse to pulse, generally in the range of 0.1 to 0.2 seconds. Since, following the initialization artifact, the detected values of Sy are within the predetermined range, each pulse in the OxiP waveform is deemed correct, i.e. unaffected by motion artifacts or other distortions. Consequently, each pulse following the initialization artifact receives a binary logic 1 in the PG tracing, which provides a visual indication as to whether each pulse waveform is good (logic 1) or bad (logic 0).

As noted above, the predetermined range of systolic upstroke times used for comparison with detected systolic upstroke times for validating pulse waveforms can be empirically derived on a single subject. Alternatively, considering that empirical observation confirms that systolic upstroke times are in a consistently narrow range from subject to subject, including infants, children and adults, a default range may be incorporated in the software thereby avoiding the necessity for establishing a range for each new subject. In initial studies to date based on observations in 5 newborns and 5 adults, a default range of 0.09–0.21 seconds has been found acceptable, and this default setting was used for generating the PG waveform in FIGS. 2–13. Of course, the software permits adjustment of the default range by the operator if visual observation confirms that "normal" pulse waveforms are being rejected as outside the default range.

In any event, once the predetermined acceptable range of systolic upstroke times is selected, the RespiEvents software compares the actual systolic tipstroke time for each successive pulse waveform with the predetermined range, and generates a pulse good (logic 1) or pulse bad (logic 0) signal on the PG tracing. Whenever PG=1, indicating that the pulse waveform is validated as confirmed by its systolic tipstroke time Sy, the corresponding arterial oxygen saturation level SaO2 is likewise deemed validated. Conversely, whenever the pulse waveform is rejected (PG=0) because its systolic upstroke time Sy falls outside of the predetermined range, the corresponding arterial oxygen saturation measurement for that pulse is also rejected. The pulse rate PR in beats per minute shown as the fourth waveform from the top in each of FIGS. 2–13 is computed as the peak to peak interval between successive pulses in the OxiP waveform. The pulse rate PR as computed from this interval is generally not as exact as the ECG heart rate due to system noise which often renders the peak of the OxiP waveform somewhat fuzzy.

Figure 3:
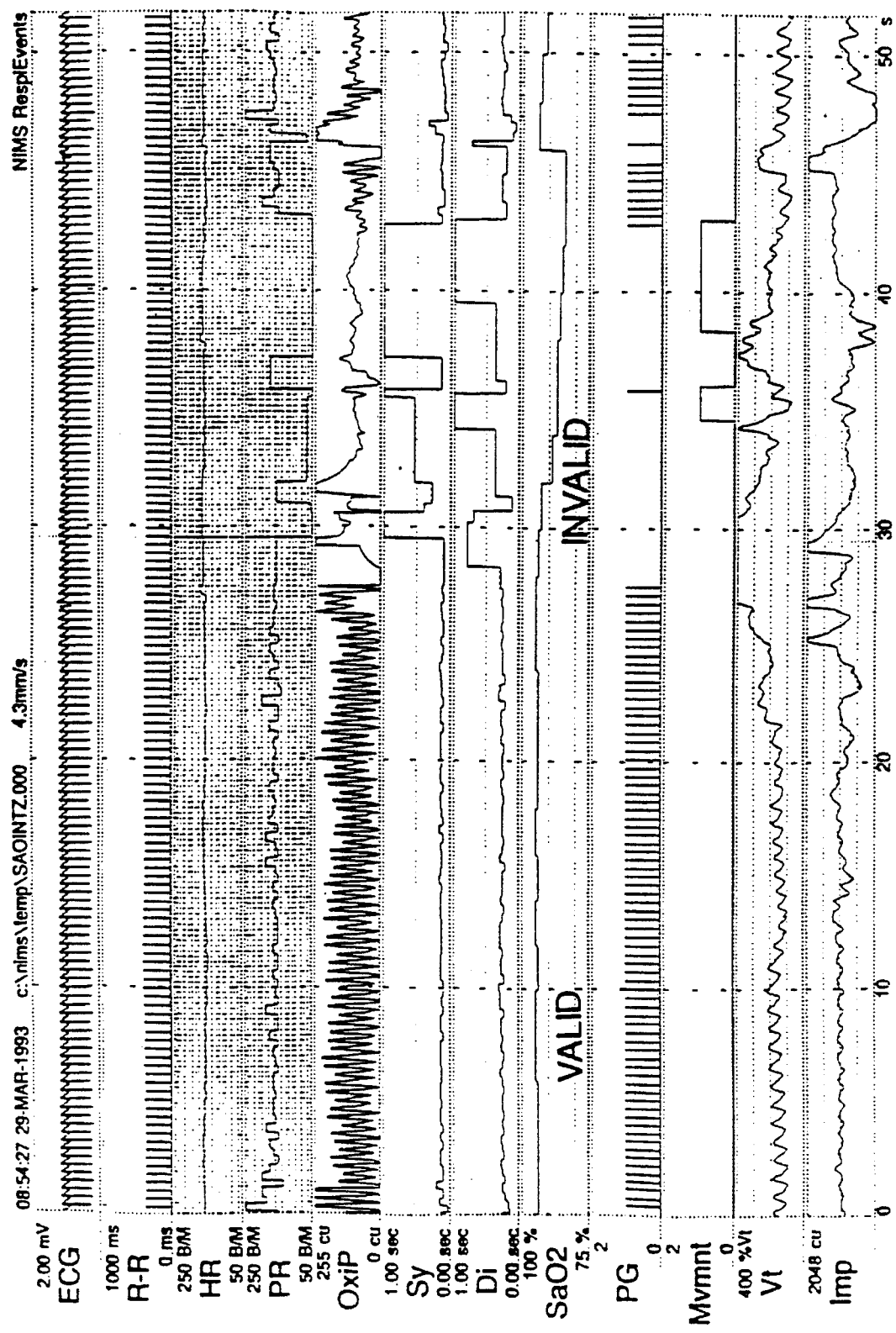

FIG. 3 is a tracing similar to FIG. 2, and illustrating both valid and invalid pulse waveforms (OxiP). During the period when the pulse waveforms appear normal, the systolic upstroke time Sy is within the acceptable range, anti the resulting pulses are deemed valid, as evidenced by the logic 1 pulses on the PG waveform. However, during periods when the pulse waveform OxiP is abnormal, the systolic tipstroke time Sy is outside of the acceptable range, and the corresponding pulses are deemed not valid, as represented by a logic 0 on the PG waveform. Again, during periods when the pulses are rejected as confirmed by the PG tracing, the corresponding arterial oxygen saturation levels are likewise rejected as invalid. FIG. 3 covers a time duration of about 50.1 seconds.

Figure 4:
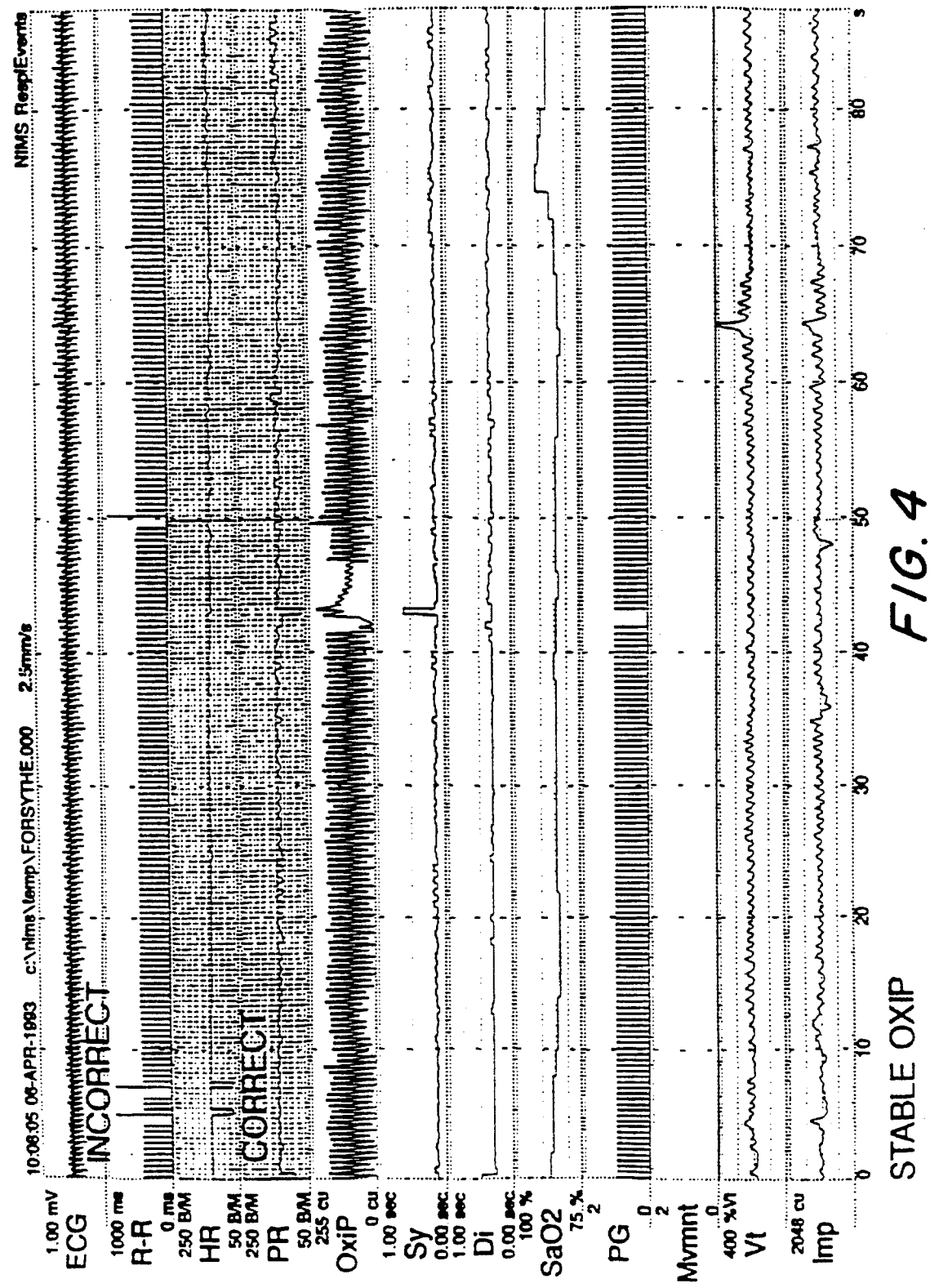

FIG. 4 is another waveform similar to FIG. 2, and covering a time duration of about 80.5 seconds. FIG. 4 is significant primarily for the leftmost portion of the tracing, wherein it may be seen that the reduced amplitude of the ECG resulted in incorrect R-R intervals and heart rate HR due to the failure of the R-wave trigger on two different heart beats. In contrast, during these heart beats, the systolic upstroke times (Sy) of the corresponding pulses on the OxiP waveform were within the predetermined range resulting in classification of these pulses as "good" (PG=1) and validation of the corresponding SaO2 measurements. The pulse rate PR derived from these pulses is, therefore, also correct.

Figure 5:
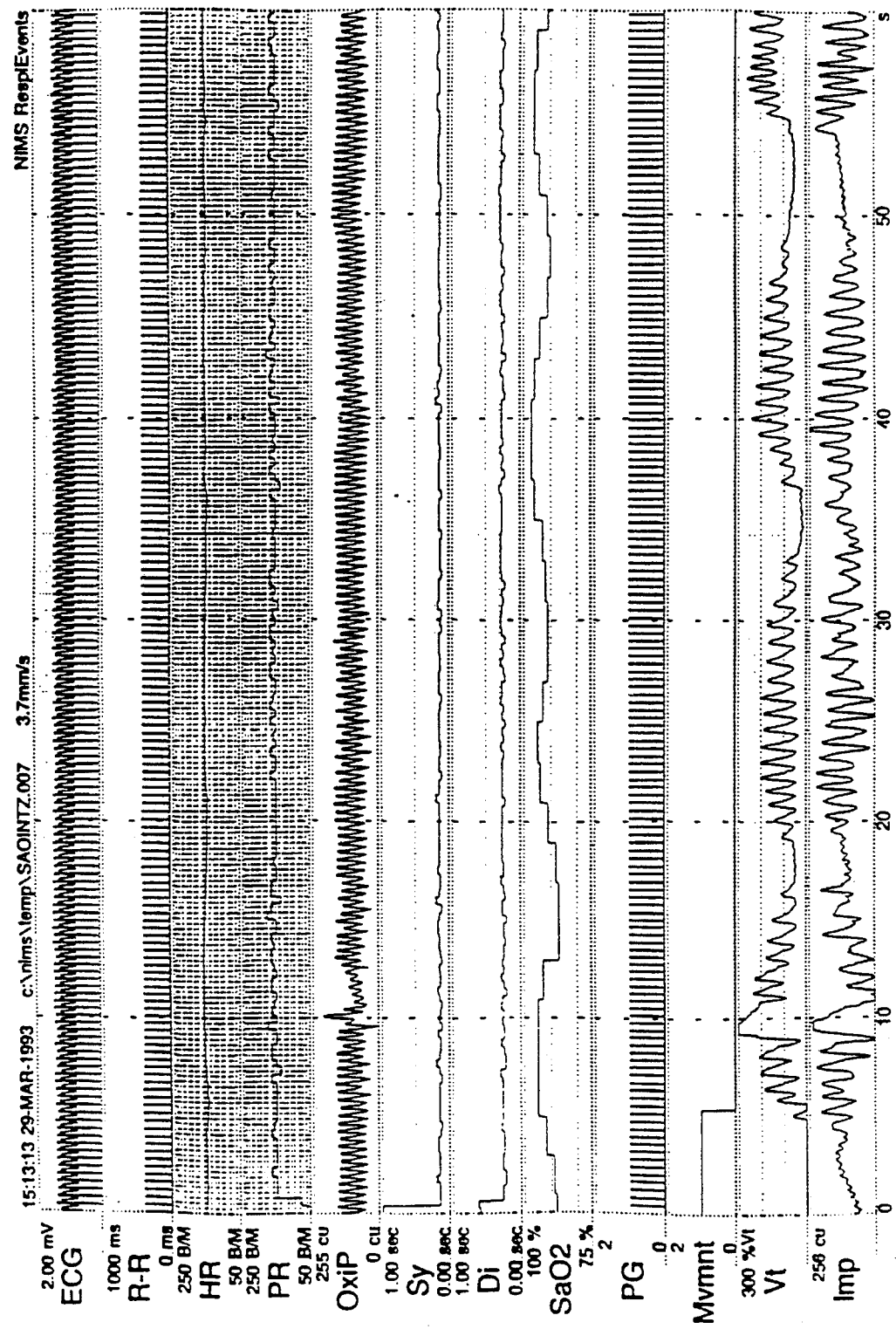

FIG. 5 is another tracing similar to FIG. 2, and covering a time duration of about 60 seconds. FIG. 5 confirms that the OxiP waveform and systolic upstroke time Sy are valid independent of breathing abnormalities, such as the periodic breathing evidenced by the oscillating Vt and hnp waveforms at the bottom of FIG. 5. That is, even during these periods of periodic breathing, the OxiP waveform is normal and the systolic upstroke time is correctly calculated as evidenced by the continuous string of "good" pulses on the PG plot.

Figure 6:
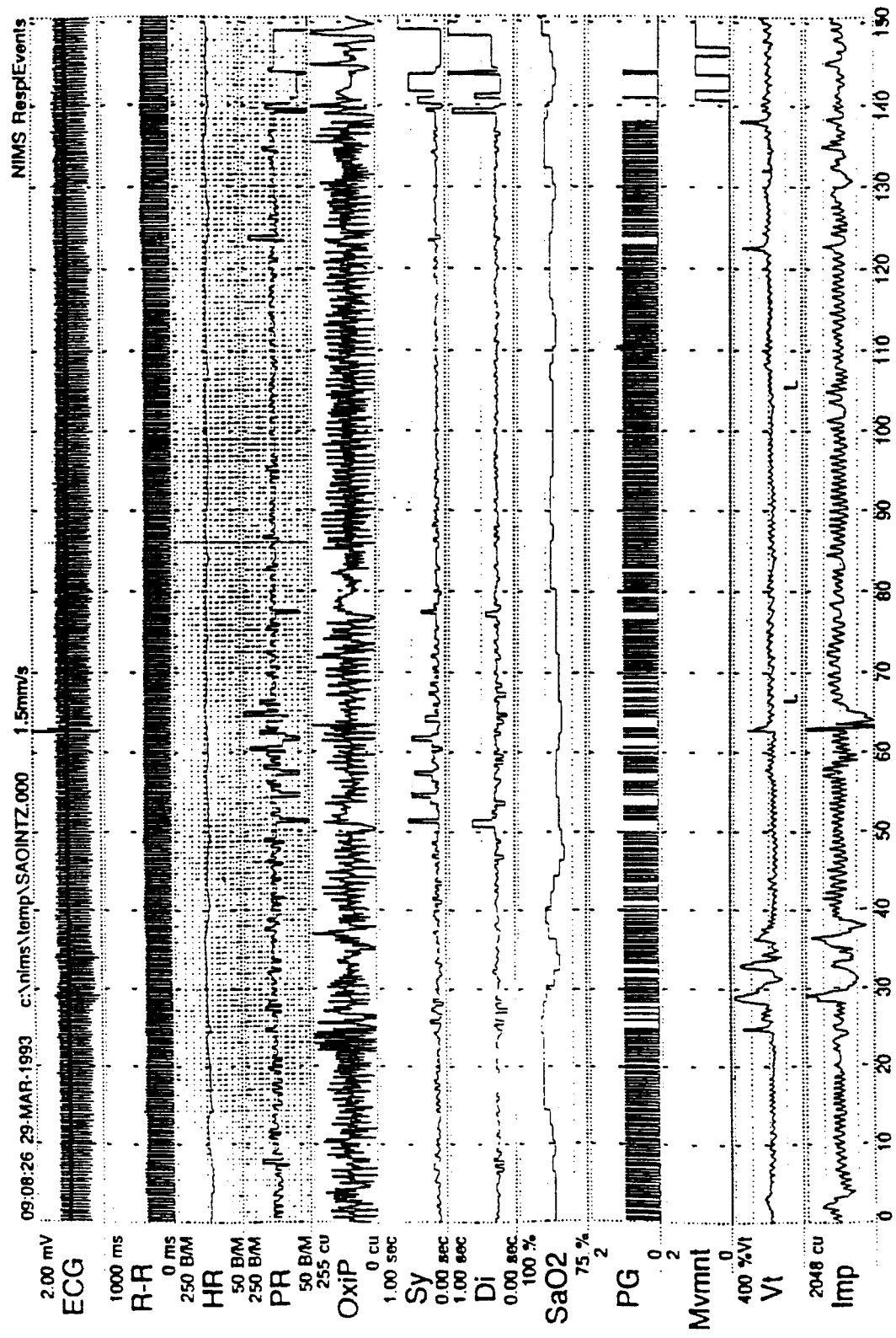

FIG. 6 is yet another waveform similar to FIG. 2 and covering a time duration of about 150 seconds. FIG. 6 is significant insofar as it confirms that systolic upstroke times are correctly calculated despite variations in the amplitude of the pulse oximeter waveform OxiP. FIG. 6 also illustrates that some of the systolic upstroke times calculated from the pulse waveform OxiP are outside the predetermined range, and hence the resulting pulses and their corresponding SaO2 waves are rejected as evidenced by intermittent logic 0 pulses on the PG waveform. The "L" on the Vt tracing denotes a labored breathing alarm generated by the inductive plethysmograph 16 and resulting from throacoabdominal incoordination.

Figure 7:
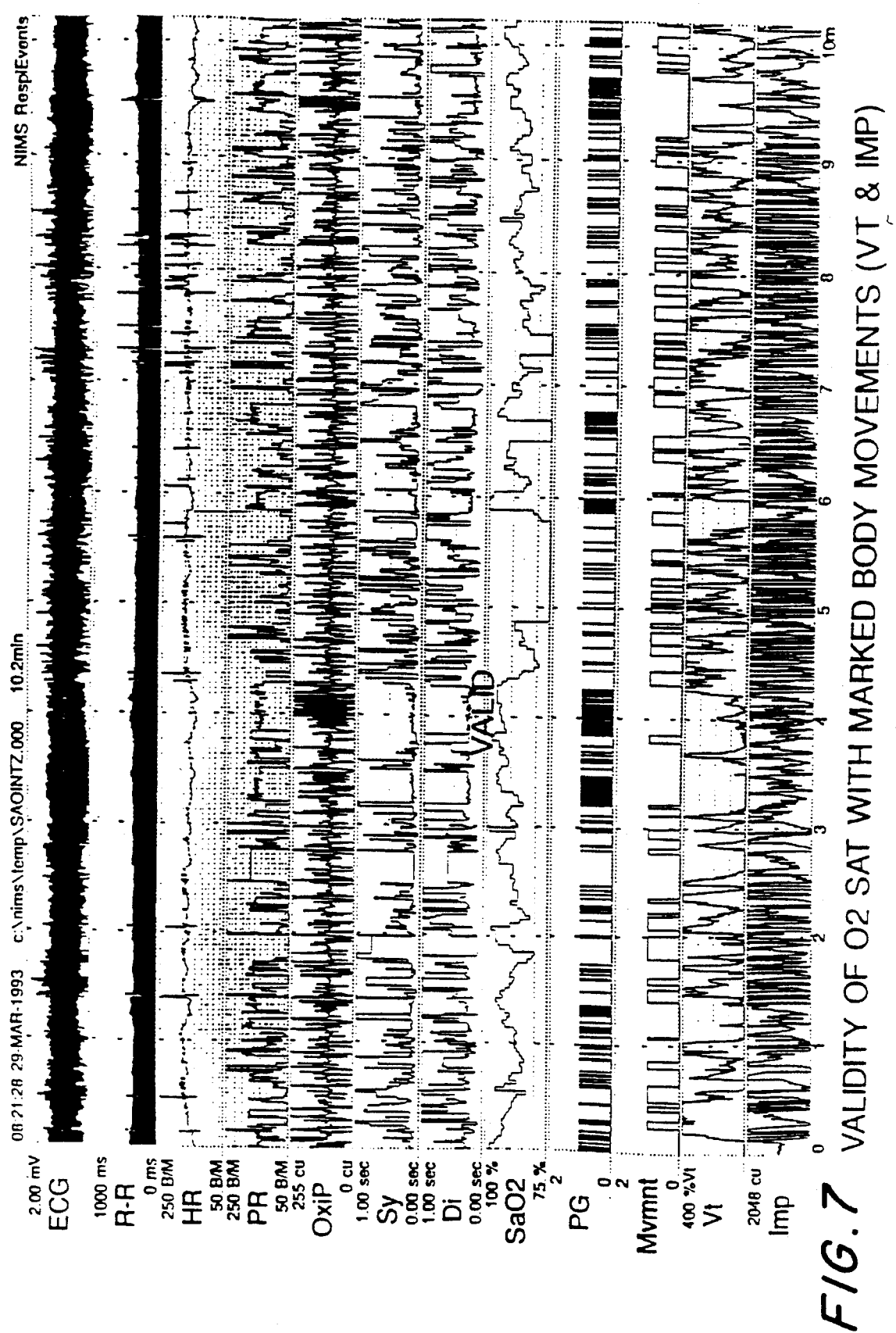

FIG. 7 is another waveform similar to FIG. 2 and covering a period of 10.2 minutes. FIG. 7 is significant insofar as it establishes that valid arterial oxygen saturation values SaO2 can be derived despite body movement evident from the significant signal oscillations on the Vt and Imp waveforms. In other words, despite body movement, the method and apparatus of the present invention for discriminating acceptable pulse waveforms (OxiP) based on systolic upstroke time permits valid arterial oxygen saturation measurements during the brief periods when the pulse oximeter sensor is stable and the systolic upstroke times are within the predetermined range as indicated, for example, by the notation "VALID" approximately in the middle of the plot of FIG. 7.

FIG. 7 also illustrates the validity of utilizing systolic upstroke times outside the predetermined range for discriminating sleep from wakefulness. Note that during periods of wakefulness, as confirmed by body movements evident from the wide band oscillations on the Vt and Imp waveforms, the systolic upstroke times Sy are also outside the predetermined range. Conversely, when the body portion to which the pulse oximeter sensor is attached is stable, indicating sleep, the systolic upstroke time is within the predetermined range. Therefore, rejected systolic upstroke times Sy, i.e. systolic upstroke times outside the predetermined range, may be relied upon alone, or in conjunction with other sensors, for discriminating wakefulness from sleep, similar to an actigraph.

Figure 8:
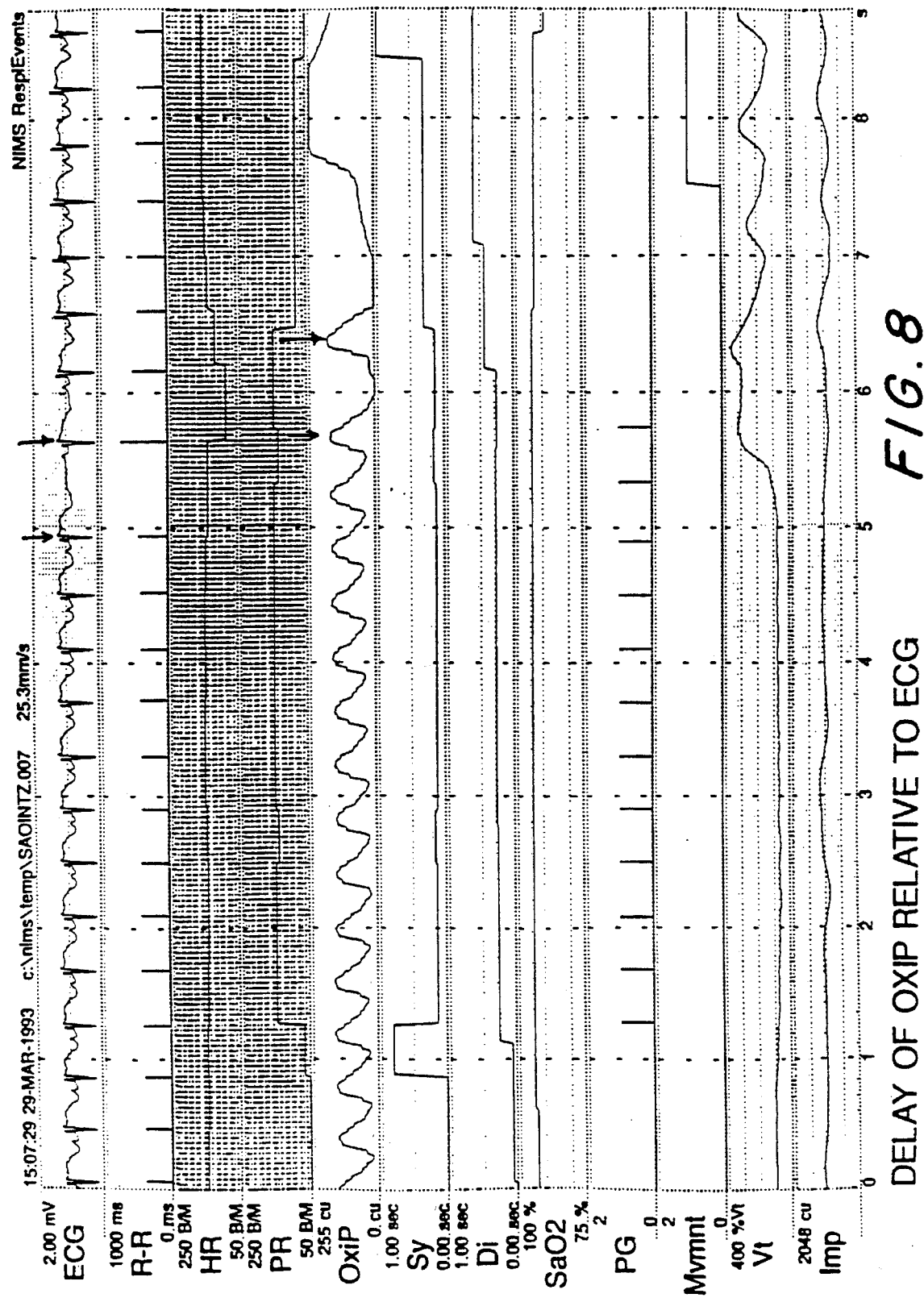

FIG. 8 is another waveform similar to FIG. 2, covering a period of about 8.7 seconds. FIG. 8. is included simply to illustrate that the pulse oximeter waveform OxiP is approximately one beat behind the ECG waveform owing to electronic filtering of the pulse oximeter waveform carried out in the pulse oximeter 12. The time lag is best seen with reference to the ECG complex noted by arrows and the two corresponding OxiP pulse waveforms, also denoted by arrows. The correspondence between the marked ECG and OxiP complexes is apparent from the time intervals between their respective peaks.

Figure 9:
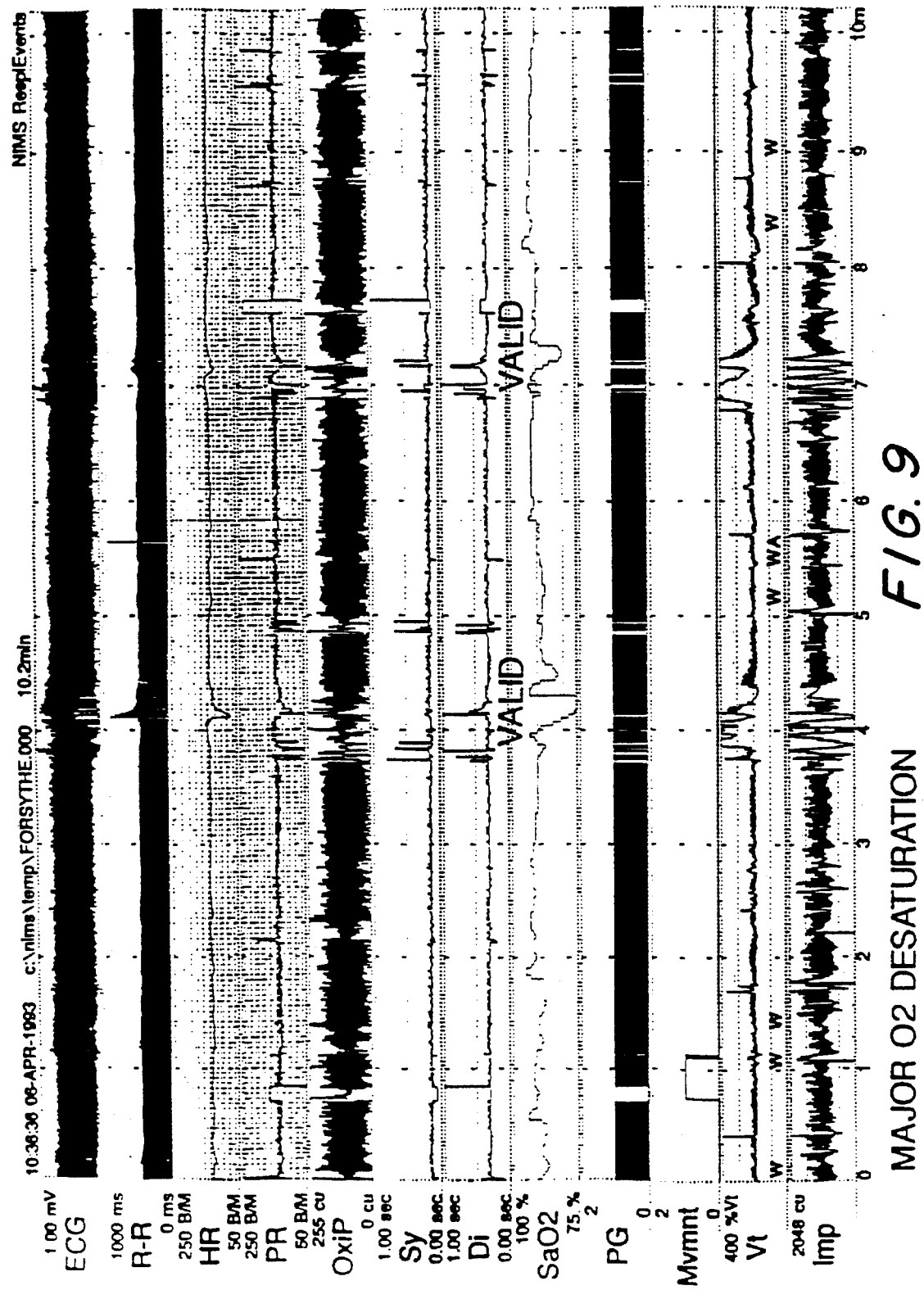

FIG. 9 is another waveform similar to FIG. 2, covering a time period of about 10.2 minutes. FIG. 9 is significant insofar as it confirms a major reduction in arterial oxygen saturation levels (SaO2) to 75% at approximately the 4 minute mark. This is confirmed because there are a significant number of acceptable pulse waveforms (OxiP) as evident from the predominance of logic 1 pulses on the PG tracing. In FIG. 9, the PG tracing appears, at times, as a solid bar because the tracing is highly condensed. The "W" and "A" markings on the Vt tracing are apnea warnings and apnea alarms, respectively, as generated by the Respitrace PT.

Figure 10:
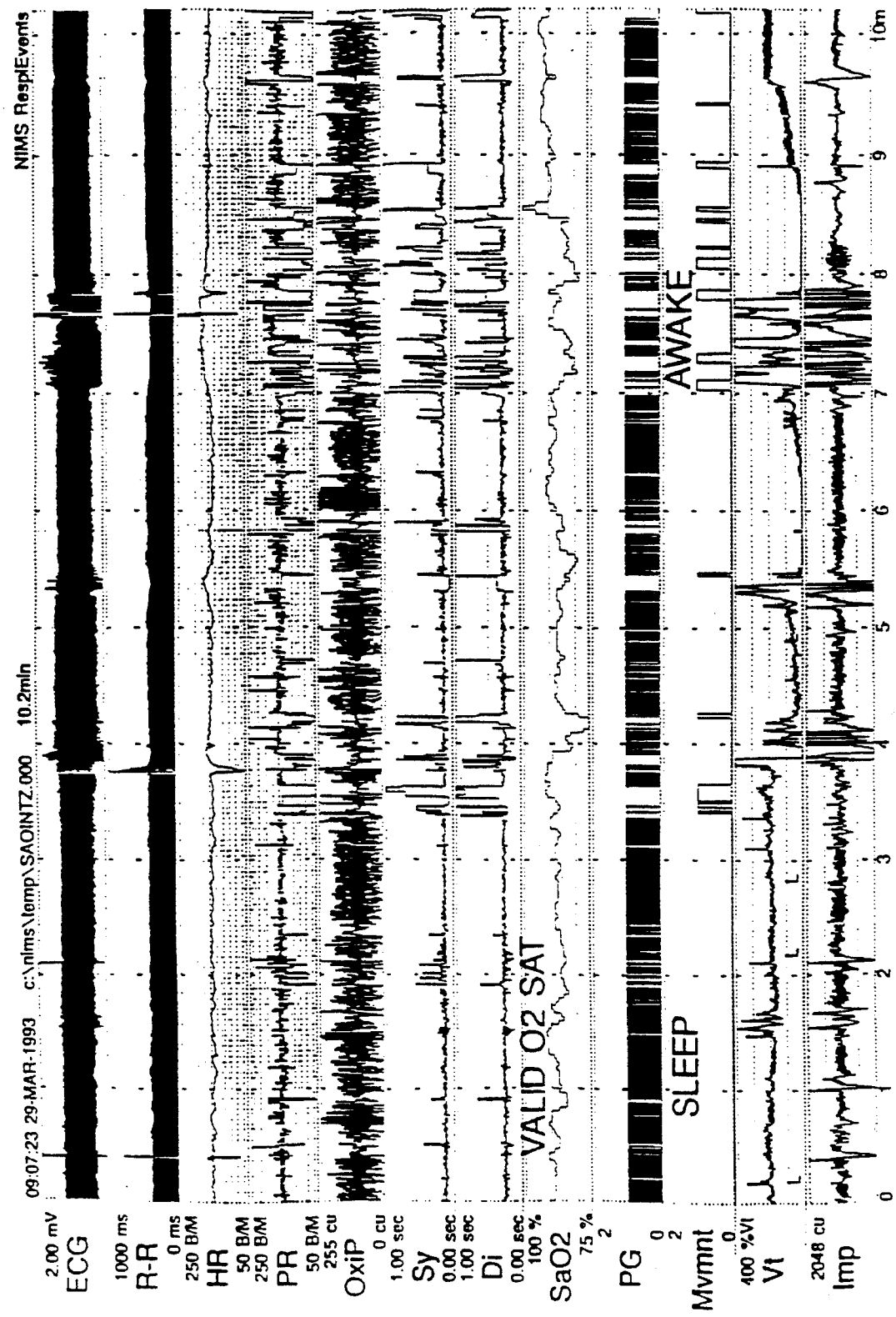

FIG. 10, another waveform similar to FIG. 2 and covering an interval of 10.2 minutes, demonstrates the manner in which the method and apparatus of the present invention may be used to differentiate wakefulness from sleep in conjunction with other sensors. In the first half of the recording, labeled "sleep", the Mvmnt waveform at approximately the 3 ½ minute mark suggests wakefulness, but this is not confirmed by the tracings on either the Vt or Imp tracings, which indicate an absence of movement. Consequently, a determination as to whether the subject is asleep or awake is inconclusive, and for purposes of analysis it may be assumed that the subject is sleeping. On the second part of the tracing, in the area marked "awake" at the 7–8 minute mark, wakefulness is confirmed by all three of the Mvmnt, Vt and Imp tracings, each of which suggests patient movement. Accordingly, the subject is confirmed as awake during this interval.

Apart from validating arterial oxygen saturation measurements and discriminating between wakefulness and sleep, another application of the method and apparatus of the present invention is for validating R-R intervals or heart rate (HR) as derived from the ECG output. R-R intervals are a useful analytical tool. For example, it has been observed that R-R intervals become quite regular prior to a loss of autonomic nervous system function that may signal the possibility of sudden cardiac death. For long term collection of R-R intervals, typically full ECG waveforms are not collected, but rather only the numerical values of the R-R time intervals are recorded to minimize storage space as on a disk, tape drive, etc. For this application, it is known to edit the recorded data for artifacts, typically caused by motion, using statistically based filters, as such artifacts render the corresponding R-R intervals unreliable. See, for example, Malik, *Heart Rate Variability in Relation to Prognosis After Myocardial Infarction: Selection of Optimal Processing Techniques*, European Heart Journal 1989; 10:1060–1074.

The method and apparatus of the present invention provides an independent basis for corroborating the validity of the R-R intervals. In this regard, simply comparing the heart rate (HR) derived from the ECG with the pulse rate (PR) as derived from a pulse oximeter is not sufficient, as this assessment does not compensate for motion artifacts introduced into the pulse waveform derived from the pulse oximeter, which artifacts can distort the pulse waveform and invalidate its measure of pulse rate.

In accordance with the method and apparatus of the present invention, R-R intervals based on the ECG can be validated by a comparison with both the pulse rate (PR) derived from the OxiP waveform and the systolic upstroke time (Sy) which, as noted hereinabove, serves as a validator for the OxiP waveform. More particularly, in accordance with the present invention, the R-R interval as calculated from the ECG is independently assessed by comparing the pulse rate (PR) as derived from the OxiP waveform with the heart rate (HR) derived from the ECG, and relying on this comparison as a validator of the R-R intervals only when the OxiP waveforms are validated by their systolic upstroke times (Sy) as discussed in greater detail hereinabove. Data from the ECG and pulse oximeter can be stored as on a disk, for subsequent verification, using an appropriate software program such as RespiEvents. Alternatively, verification can be done in real time, with only valid R-R intervals being stored, in which event the pulse oximeter or related equipment may be equipped with warnings and/or alarms based on the trend of validated R-R intervals, e.g. if the R-R intervals become regular or indicate bradycardia or tachycardia.

In accordance with the present invention, R-R intervals can be validated as follows: (1) if the pulse rate (PR) as derived from the OxiP waveform is close to the heart rate (HR) measured with an ECG and the systolic upstroke times (Sy) of the OxiP waveforms are within the predetermined range, then the corresponding R-R intervals are deemed valid; (2) if the pulse rate (PR) derived from the OxiP waveform markedly differs from the heart rate (HR), and the corresponding systolic upstroke times (Sy) fall outside of the predetermined range, the validity of the R-R intervals is uncertain, as it is possible that the pulse rate (PR) results from movement artifacts, in which event the R-R intervals could be valid, though it is also possible that the R-R intervals are invalid as there is no independent confirmation; (3) if the pulse rate (PR) derived from the OxiP waveform is close to the heart rate (HR) from the ECG but the systolic upstroke times (Sy) are outside the valid range, then again the R-R intervals cannot be considered validated, since the validity of the OxiP pulse waveform is not validated by the systolic upstroke time (Sy), and hence the comparison between the pulse rate (PR) derived from the OxiP waveform and the heart rate (HR) cannot be presumed valid; and (4) if the pulse rate (PR) derived from the OxiP waveform differs markedly from the heart rate (HR) and the systolic upstroke time (Sy) falls within the predetermined range, the R-R intervals again cannot be confirmed as valid, since this suggests that the pulse rate (PR) derived from the OxiP waveform is valid as confirmed by the systolic upstroke times (Sy), which in turn suggests that the R-R intervals are not valid.

It should be recognized, of course, that this analysis might exclude legitimate R-R interval values in the event the pulse oximeter is not operating correctly when the ECG signal is valid. However, if all three conditions are met, i.e. the heart rate (HR) derived from the ECG is close to the pulse rate (PR) derived from the OxiP waveform, and the OxiP waveform is confirmed as valid by systolic upstroke times (Sy) within the predetermined range, then the operator can be confident that the corresponding R-R intervals are valid.

Of course, while the foregoing description addresses validating R-R intervals derived from the ECG, the methodology is equally applicable to verifying the heart rate (HR) as measured by the ECG, since the R-R interval is simply the time interval between successive R-wave peaks. This is illustrated below with reference to FIGS. 11–13.

Figure 11:
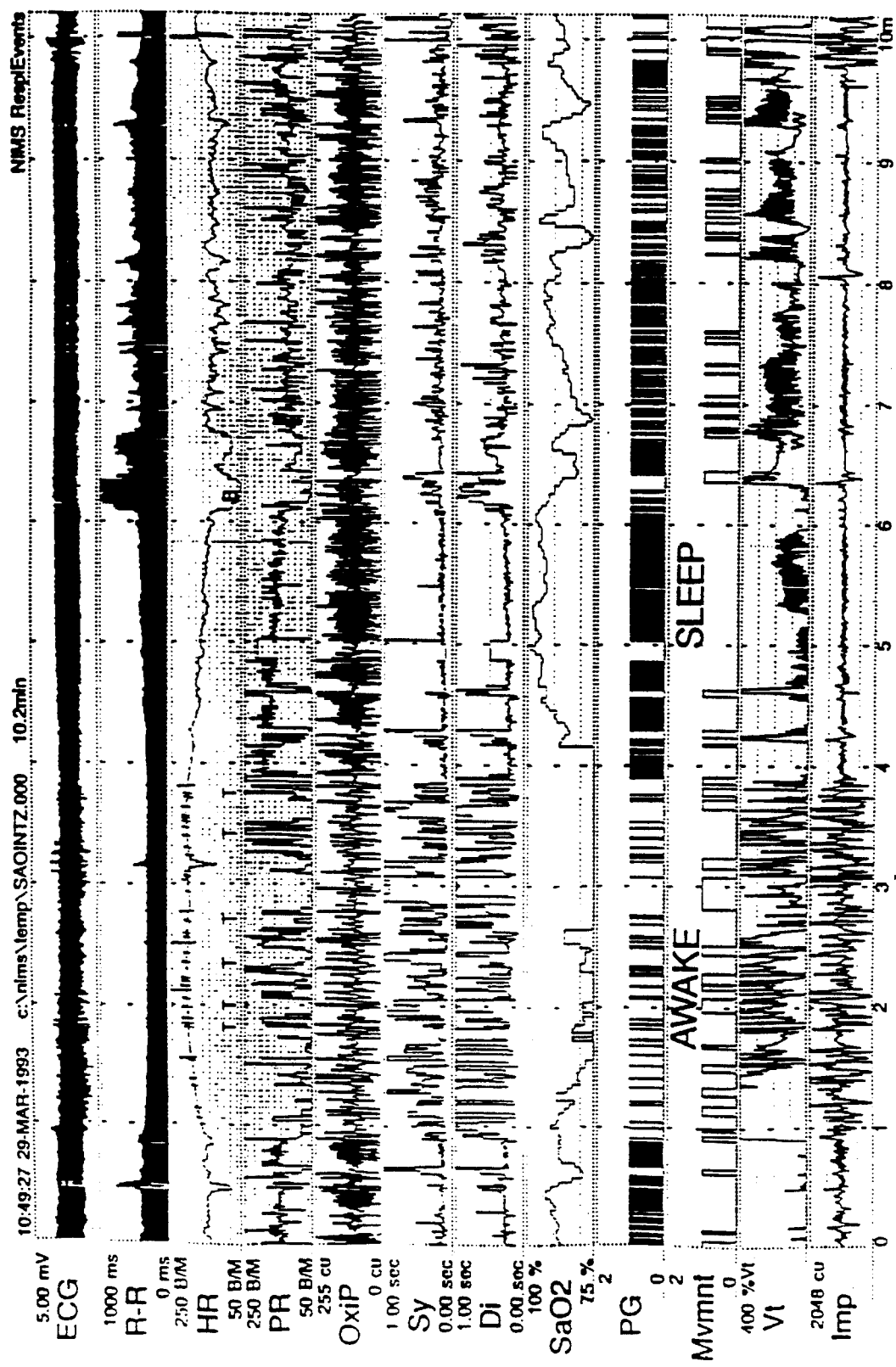

FIG. 11 is yet another waveform similar to FIG. 2 and covering a time period of 10.2 minutes. FIG. 11 demonstrates the use of the method and apparatus of the present invention to verify bradycardia, i.e. a slowing of the heart rate. In FIG. 11, the bradycardia is noted by a "B" on the HR tracing at approximately the 6:20 marker. The bradycardia is considered confirmed since during the bradycardia the systolic upstroke times (Sy) measured from the pulse oximeter waveform (OxiP) are within the predetermined range as confirmed by the logic 1 pulses on the PG tracing. Furthermore, the pulse rate (PR) of the OxiP pulse waveform as shown on the PR tracing is approximately the same as the heart rate (HR) derived from the ECG and shown on the HR tracing. The periods of tachycardia marked by a "T" on the HR tracing are not considered confirmed, since many of the rapid beats were recorded during periods when the pulse oximeter waveform OxiP was deemed unacceptable based on its systolic upstroke times, as confirmed by the logic 0 pulses on the PG waveform. In other words, the pulse oximetry data cannot be deemed reliable during these intervals and hence cannot validate the heart rate as derived from the ECG.

Figure 12:
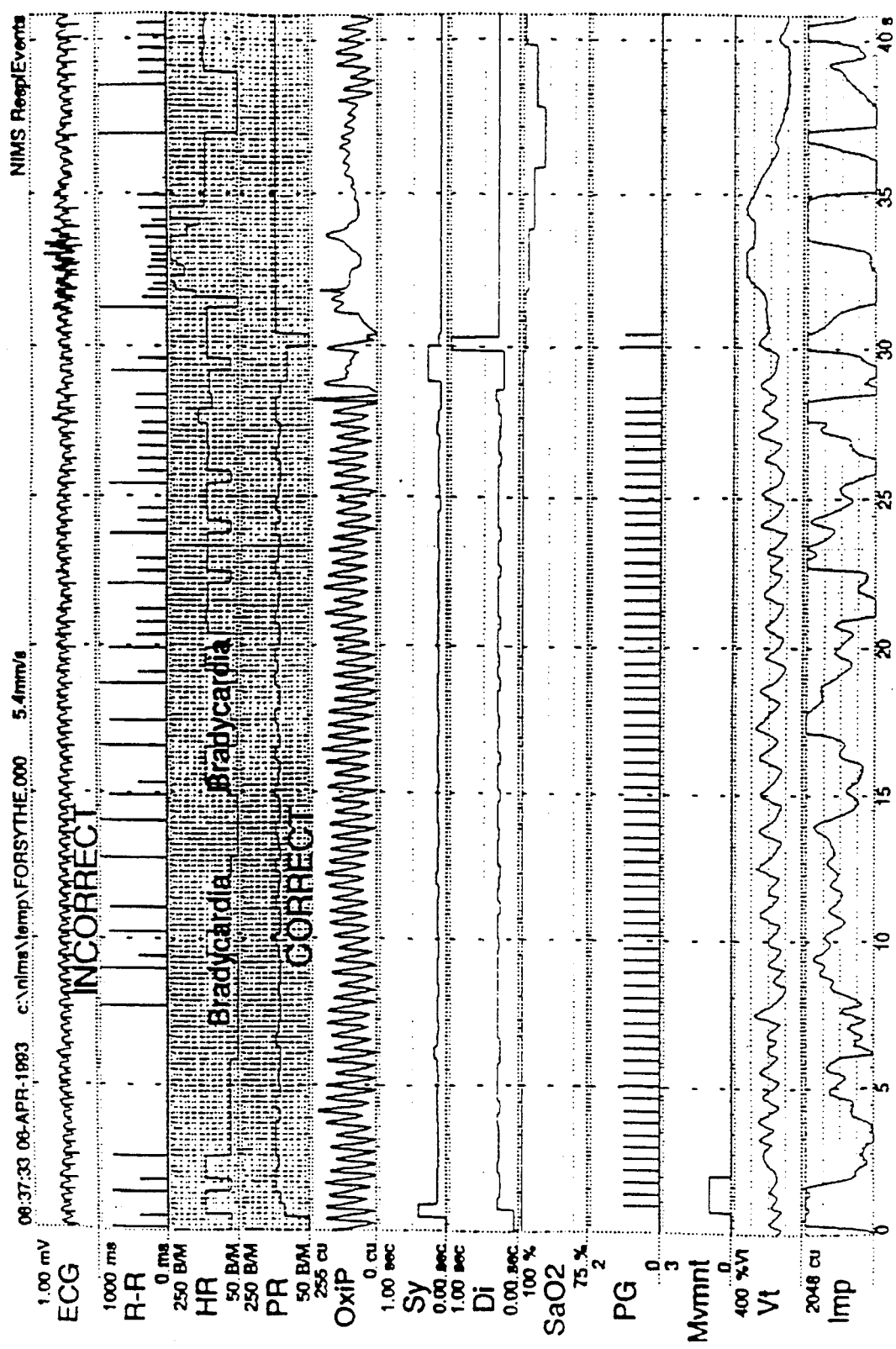

FIG. 12 is another waveform similar to FIG. 2 showing a time plot having a duration of about 40 seconds. FIG. 12 demonstrates use of the method and apparatus of the present invention to verity cardiac arrhythmia as derived from the ECG. In FIG. 12, the ECG recording suggests a bradycardia. However, during the same interval, the pulse waveforms derived from the pulse oximeter (OxiP) are mostly normal, as suggested by the logic 1 pulses on the PG waveform. This suggests that the bradycardia detected by the ECG is unreliable, and that the correct pulse rate is the one determined by the peak to peak intervals on the OxiP recording, i.e. the pulse rate tracing PR. Analysis of the ECG waveform shows that it is of extremely low amplitude and that the false bracycardia on the HR tracing resulted from the failure of the ECG's R-wave trigger to detect a heart beat. This may result, for example, from a high skin impedance at the point of electrode contact, which is common in long term monitoring. In FIG. 12, for the same reason that the heart rate (HR) as calculated by the ECG is unreliable, the R-R intervals based on the ECG are also unreliable.

Figure 13:
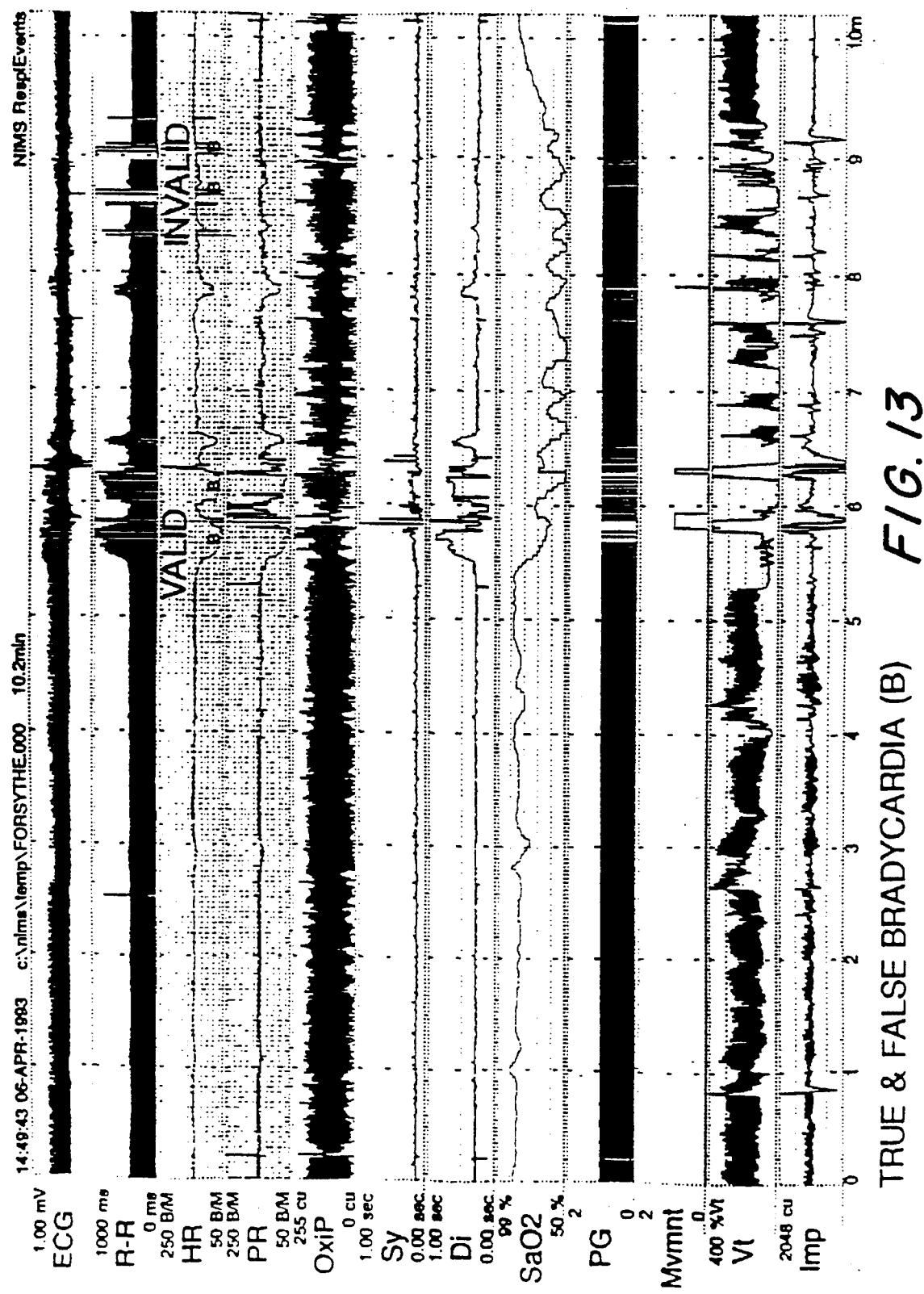

FIG. 13 is another waveform similar to FIG. 2 and showing a time plot of about 10.2 minutes duration. FIG. 13 also demonstrates the manner in which the method and apparatus of the present invention are used to confirm cardiac arrhythmia by comparing the pulse oximeter waveform OxiP with the ECG. In particular, referring to the first bradycardia event at approximately the 6 minute mark, this bradycardia is deemed valid because the pulse rate (PR) derived from the OxiP waveform corresponds to the heart rate (HR) as detected by the ECG and, in addition, there are a significant number of "good" pulse waveforms during the event, as demonstrated by the logic 1 pulses on the PG waveform at the 6 minute mark. Looking next at the bradycardia event at the 9 minute mark, that bradycardia is deemed invalid, i.e. not confirmed, because the pulse rate (PR) as derived from the Oxip waveform differs markedly from the reduced heart rate (HR) detected by the ECG, and the OxiP waveform is deemed valid during this interval as confirmed by the logic 1 pulses on the PG waveform.

Thus far, and as is preferred, the pulse waveform (OxiP) generated by the pulse oximeter is validated with reference to the systolic upstroke time (Sy). Alternatively, the diastolic time of the pulse waveforms may be utilized. However, this is not preferred because while diastolic times are reliable in subjects with regular cardiac rhythms, they become variable in the presence of cardiac arrhythmia.

As noted hereinabove, the apparatus 10 depicted in FIG. 1 was intended primarily for verifying the methodology of the present invention though, of course, it can also be used for practicing the invention. Where the invention is used simply as a validator of pulse oximetry data, much of the apparatus shown in FIG. 1 can be dispensed with. In particular, it is contemplated that the invention may be used with a conventional pulse oximeter modified to incorporate the teachings of the present invention. In this regard, it is well within the capabilities of a person of ordinary skill in the art who has read this description to modify a conventional pulse oximeter to calculate the systolic upstroke time of the pulse waveform and compare that systolic upstroke time, as on a pulse by pulse basis, with a predetermined range. It is similarly within the capabilities of the person of ordinary skill in the art to modify a conventional pulse oximeter to incorporate a predetermined default range of systolic upstroke times, such as about 0.09 seconds to about 0.21 seconds, and for permitting operator modification of this predetermined range based on empirical observation for the monitored subject as described hereinabove. A pulse oximeter modified in this fashion may also be used with an ECG to validate the heart rate (HR) and R-R intervals derived by the ECG, also as more fully explained above. Similarly, such a modified pulse oximeter may also be used to discriminate sleep from wakefulness, also as described hereinabove, either alone or in conjunction with other sensors indicative of skeletal muscle movement, such as a respiratory inductive plethysmograph. A conventional pulse oximeter modified as suggested herein may, of course, include a storage medium for storing pulse waveforms (OxiP), systolic tipstroke times (Sy), pulse rate (PR), etc. for subsequent analysis. All such data may be stored or, alternatively, only data corresponding to validated pulse waveforms.

It is also within the capabilities of a person of ordinary skill in the art who has read this description to modify a conventional pulse oximeter to include visual and/or audio signals for advising the operator of the presence of rejected pulse waveforms, low arterial oxygen saturation levels, low pulse rate, etc.

It should be understood that the preferred embodiments and examples described are for illustrative purposes only and are not to be construed as limiting the scope of the present invention which is properly delineated only in the appended claims.

What is claimed is:

1. A method for discriminating between artifactual and non-artifactual pulse waveforms generated by a pulse oximeter for validating indicated arterial oxygen saturation levels of a subject also generated by the pulse oximeter, the pulse waveforms each being defined, at least partially, by a systolic upstroke time and a diastolic time, the method comprising:

selecting a predetermined range of a first parameter indicative of a correct pulse waveform, said first parameter being selected from the group consisting of systolic upstroke times and diastolic times;

receiving from the pulse oximeter, in a first receiving step, pulse waveforms;

receiving from the pulse oximeter, in a second receiving step, signals indicative of the arterial oxygen saturation level of the subject;

measuring said first parameter of the received pulse waveforms, wherein said measuring step comprises measuring the systolic upstroke times corresponding to received pulse waveforms;

comparing the measured systolic upstroke times to a predetermined range of, systolic upstroke times;

rejecting as artifactual any of the pulse waveforms having a systolic upstroke time outside said predetermined range of systolic upstroke times; and determining the arterial oxygen saturation levels indicated by the received signals corresponding temporally to the non-rejected pulse waveforms.

2. The method of claim 1, wherein said predetermined range is determined to be from about 0.09 seconds to about 0.21 seconds.

3. The method of claim 1, wherein said received pulse waveforms and signals correspond to output by a pulse oximeter, said method further comprising rejecting arterial oxygen saturation levels of the subject determined from said signals received during time periods respectively corresponding to rejected pulse waveforms.

4. The method of claim 3, wherein said step of rejecting said arterial oxygen saturation levels comprises rejecting said arterial oxygen saturation levels on a real time basis.

5. The method of claim 4, further comprising the step of storing arterial saturation levels derived from signals generated by the pulse oximeter during times other than those respectively corresponding to rejected pulse waveforms.

6. The method of claim 1, further comprising a step of generating pulse waveforms, the pulse waveforms each being defined, at least partially, by a systolic upstroke time and a diastolic time, with a pulse oximeter prior to said first receiving step.

7. The method of claim 1, further comprising the steps of monitoring said subject for generating a signal indicative of a heart rate of the subject; determining a pulse rate from the received pulse waveforms; and validating the heart rate of the subject only when the pulse rate of the non-rejected pulse waveforms is approximately equal to the heart rate indicated by said signal.

8. A method for discriminating between artifactual and non-artifactual pulse waveforms for validating indicated arterial oxygen saturation levels of a subject, the pulse waveforms each being defined, at least partially, by a systolic upstroke time and a diastolic time, the method comprising:

receiving pulse waveforms;

measuring, in a first measuring step, a first parameter of the received pulse waveforms selected from the group consisting of the systolic upstroke times and diastolic times;

comparing the measured first parameter to a predetermined range of the first parameter indicative of a correct pulse waveform;

rejecting as artifactual any of the received pulse waveforms having a said measured first parameter outside said predetermined range of the first parameter;

measuring, in a second measuring step, the first parameter for as plurality of pulse waveforms generated prior to said first measuring step; and determining said predetermined range from selected first parameter values measured during said second measuring step, wherein said step of determining said predetermined range comprises:

determining a second parameter selected from a mean and median of the selected first parameter for said plurality of pulse waveforms of said second measuring step, and establishing said predetermined range as within a predetermined time interval having a minimum less than said second parameter and a maximum greater than said second parameter.

9. The method of claim 8, further comprising the step of verifying that said plurality of pulse waveforms have normal waveforms.

10. A method for discriminating between artifactual and non-artifactual pulse waveforms for validating indicated arterial oxygen saturation levels of a subject, the pulse waveforms each being defined, at least partially, by a systolic upstroke time and a diastolic time, the method comprising:

receiving pulse waveforms;

measuring a first parameter of the received pulse waveforms selected from the group consisting of the systolic upstroke times and diastolic times;

comparing the measured first parameter to a predetermined range of the first parameter indicative of a correct pulse waveform;

rejecting as artifactual any of the pulse waveforms having a said measured first parameter outside said predetermined range of the first parameter; and determining whether said subject is asleep or awake by classifying said subject as awake during time intervals corresponding to rejected pulse waveforms and as asleep during time intervals corresponding to non-rejected pulse waveforms.

11. The method of claim 10, further comprising the step of monitoring said subject's breathing and wherein said classifying step comprises classifying said subject as awake only when said rejected pulse waveforms persist for at least one breath.

12. A method for discriminating between artifactual and non-artifactual pulse waveforms for validating a heart rate of a subject, the pulse waveforms each being defined, at least partially, by a systolic upstroke time and a diastolic time, the method comprising:

receiving pulse waveforms;

measuring a first parameter of the received pulse waveforms selected from the group consisting of the systolic upstroke times and diastolic times;

comparing the measured first parameter to a predetermined range of the first parameter indicative of a correct pulse waveform;

rejecting as artifactual any of the pulse waveforms having a said measured first parameter outside said predetermined range of the first parameter;

monitoring said subject with an ECG for generating a signal indicative of the heart rate of the subject;

determining a pulse rate from pulse waveforms not rejected at said rejecting step; and validating the heart rate of the subject only when the pulse rate of the non-rejected pulse waveforms is approximately equal to the heart rate.

13. The method of claim 12, wherein said step of validating said heart rate further comprises validating said heart rate on a real time basis.

14. The method of claim 13, further comprising the step of storing data corresponding to the heart rate when the heart rate is validated.

15. The method of claim 12, wherein said step of validating the heart rate of the subject further comprises validating R-R intervals of the subject.

16. An apparatus for discriminating between artifactual and non-artifactual pulse waveforms for validating indicated arterial oxygen saturation levels of a subject, the pulse waveforms each being defined, at least partially, by a systolic upstroke time and a diastolic time, the apparatus comprising:

means for selecting a predetermined range of a first parameter indicative of a correct pulse waveform, said selecting means selecting said first parameter from the group consisting of systolic upstroke times and diastolic times;

first means for receiving pulse waveforms;

second means for receiving signals indicative of the arterial oxygen saturation level of the subject;

means for measuring said first parameter of the pulse waveforms received by said first receiving means, wherein said means for measuring is operative to measure systolic upstroke times of the received pulse waveforms;

means for comparing the measured systolic upstroke times to the predetermined range of systolic upstroke times selected by said selecting means;

means for rejecting as artifactual any of the received pulse waveforms corresponding to measured systolic upstroke times outside said predetermined range of systolic upstroke times; and means for determining the arterial oxygen saturation levels indicated by the received signals corresponding temporarily to the non-rejected pulse waveforms.

17. The apparatus of claim 16, wherein said predetermined range is from about 0.009 seconds to about 0.21 seconds.

18. The apparatus of claim 16, wherein said received pulse waveforms and signals correspond to output by a pulse oximeter, said apparatus further comprising means for rejecting arterial oxygen saturation levels of the subject determined from said signals received during time periods corresponding to respective rejected pulse waveforms.

19. The apparatus of claim 18, wherein said means for rejecting said arterial oxygen saturation levels is operative to reject said arterial oxygen levels on a real time basis.

20. The apparatus of claim 19, further comprising means for storing arterial oxygen saturation levels derived from said signals generated by the pulse oximeter during times other than those corresponding to rejected pulse waveforms.

21. The apparatus of claim 16, further comprising a pulse oximeter for generating at least some of the pulse waveforms received by said first receiving means.

22. The apparatus of claim 16, wherein the received pulse waveforms correspond to output by a pulse oximeter, said apparatus further comprising means for generating a signal indicative of a heart rate of the subject; means for determining a pulse rate from the received pulse waveforms; and means for indicating that the pulse rate of the non-rejected pulse waveforms is approximately equal to the heart rate indicated by said signal.

23. An apparatus for discriminating between artifactual and non-artifactual pulse waveforms for validating indicated arterial oxygen saturation levels of a subject the pulse waveforms each being defined, at least partially, by a systolic upstroke time and a diastolic time, the apparatus comprising:

means for receiving pulse waveforms;

first means for measuring a first parameter of said received pulse waveforms, said measured first parameter being selected from the group consisting of the systolic upstroke times and diastolic times;

second means for measuring the first parameter for a plurality of waveforms generated prior to the pulse waveforms received by said first means for receiving;

means for determining a predetermined range of the first parameter indicative of a correct pulse waveform from said measured first parameter of said pulse waveforms, wherein said means for determining said predetermined range is operative to determine one of a mean and median of said selected one of said systolic upstroke times and diastolic times for said prior generated plurality of pulse waveforms and to establish as said predetermined range a predetermined time interval having a minimum less than one of said mean and median and a maximum greater than one of said mean and median;

means for comparing the measured first parameter of said pulse waveforms to said predetermined range of the first parameter; and means for rejecting as artifactual any of the received pulse waveforms having a said measured first parameter outside said predetermined range of the first parameter.

24. The apparatus of claim 23, further comprising means for verifying that said prior generated plurality of pulse waveforms have normal waveforms.

25. An apparatus for discriminating between artifactual and nonartifactual pulse waveforms for validating indicated arterial oxygen saturation levels of a subject, the pulse waveforms each being defined, at least partially, by a systolic upstroke time and a diastolic time, the apparatus comprising:

means for receiving pulse waveforms;

means for measuring a first parameter of said received pulse waveforms, said measured first parameter being selected from the group consisting of the systolic upstroke times and diastolic times;

means for comparing the measured first parameters to a predetermined range of the first parameter indicative of a correct pulse waveform;

means for rejecting as artifactual any of the received pulse waveforms having a said measured first parameter outside the predetermined range of the first parameter; and means for classifying said subject as awake during first time intervals corresponding to rejected pulse waveforms and as asleep during second time intervals corresponding to non-rejected pulse waveforms.

26. The apparatus of claim 25, further comprising means for monitoring said subject's breathing and wherein said means for classifying comprises means for classifying said subject as awake only when said rejected pulse waveforms persist for at least one breath.

27. The apparatus of claim 26, wherein said indicating means is operative to indicate, on a real-time basis, that the pulse rate of non-rejected pulse waveforms is approximately equal to the heart rate.

28. The apparatus of claim 27, furthe comprising means for storing data corresponding to the heart rate when the heart rate is approximately equal to the pulse rate.

29. An apparatus for discriminating between artifactual and non-artifactual pulse waveforms for validating a heart rate of a subject, the pulse waveforms each being defined, at least partially, by a systolic upstroke time and a diastolic time, the apparatus comprising:

means for receiving the pulse waveforms corresponding to pulse signals output by a pulse oximeter;

means for measuring a first parameter of said received pulse waveforms selected from the group consisting of the systolic upstroke times and diastolic times;

means for comparing the measured first parameter to a redetermined range of the first parameter indicative of a correct pulse waveform;

means for rejecting as artifactual any of the received pulse waveforms having a said measured first parameter outside said predetermined range of the first parameter;

an ECG for generating a signal indicative of a heart rate of the subject;

means for determining a pulse rate from the pulse waveforms generated by the pulse oximeter; and means for indicating that the pulse rate of non-rejected pulse waveforms is approximately equal to the heart rate.

* * * * *